(12) United States Patent
Ding

(10) Patent No.: US 9,574,188 B2
(45) Date of Patent: Feb. 21, 2017

(54) DNA RESTRICTION LIBRARY TAGGING AND ANALYSIS

(71) Applicant: Harborgen Biotech LLC, Cockeysville, MD (US)

(72) Inventor: Dacheng Ding, Cockeysville, MD (US)

(*) Notice: Subject to any disclaimer, the term of this patent is extended or adjusted under 35 U.S.C. 154(b) by 303 days.

(21) Appl. No.: 14/230,085

(22) Filed: Mar. 31, 2014

(65) Prior Publication Data

US 2015/0275297 A1 Oct. 1, 2015

(51) Int. Cl.
*C12Q 1/68* (2006.01)
*C12N 15/10* (2006.01)

(52) U.S. Cl.
CPC ......... *C12N 15/1065* (2013.01); *C12Q 1/6855* (2013.01)

(58) Field of Classification Search
None
See application file for complete search history.

*Primary Examiner* — David Thomas
(74) *Attorney, Agent, or Firm* — Ming Chow; Sinorica, LLC

(57) ABSTRACT

The disclosed methods in the application relates to making an adapter-tagged restriction library. The library or libraries created with the disclosed methods avoid the self-ligation of the restriction fragments. The application further disclosed methods of using the library or libraries to measure the methylation level of a genome, or comparing methylation levels among two or more genomes. The measurement of the global methylation levels can be achieved with quantitative PCR method by measuring the number of restriction fragments in the libraries. It also can be used for next generation Sequencing (NGS), Copy Number Variation (CNV), restriction site mutation, endogenous gene jumping, and exogenous DNA insertion, somatic hypermutation, gene knockout/knock in etc.

19 Claims, 9 Drawing Sheets

DNA RESTRICTION LIBRARY TAGGING AND ANALYSIS

FIELD OF INVENTION

The present invention generally relates to genetics and molecular biology. Specifically, the invention relates to methods for genomic DNA restriction fragments shearing, tagging, and the tagged restriction fragments analysis.

SEQUENCE LISTING

The instant application contains a Sequence Listing which has been submitted in ASCII format via EFS-Web and is hereby incorporated by reference in its entirety. Said ASCII copy, created on Mar. 21, 2014, is named Harborgen042726.0101.txt, and is 597 bytes in size.

BACKGROUND

Genomic DNA molecules contain methylated bases in vivo. Such methylation affects a number of physiological functions, such as gene expression. DNA Methylation also carries important pathological consequences, which explains why it became an important research topic in recent years. For example, studies have found that DNA methylation levels differ between normal tissue and cancer tissue. In addition to its implication in cancer, DNA methylation also plays important roles in epigenetic inheritance, embryonic development, postnatal development, as well as bacteria host defense.

Given the importance of DNA methylation, it is crucial to accurately measure the methylation level of a given genomic DNA, or compare the methylation levels between genomic DNA samples. The large size of genomic DNA is difficult to manipulate and study as a whole. The digestion of genomic DNA to smaller pieces by restriction enzymes is one of the commonly used methods. The DNA fragment mixture after restriction enzyme digestion is defined as restriction library. Accurate measurement of genomic DNA methylation level can be reached through accurately tagging the restriction library and subsequently amplifying them in a faithful fashion. Methylation Sensitive Restriction Enzyme (MSRE) play an important role in the analysis of DNA methylation, but traditional methods of tagging the restriction library suffer because of the inaccuracies in ligation process, which is mainly caused by the self-ligation of the restriction fragments. There exists an urgent need for a better and more accurate method of breaking down and amplifying the genomic DNA, as well as accurately measuring the methylation level of one genomic DNA, or comparing the methylation levels between two genomic DNA samples.

SUMMARY

The present application relates to a method of making an adapter-tagged restriction library comprising: providing a double-stranded DNA oligonucleotide ("twin adapter") containing a recognition site of a first restriction enzyme ("first RE"); digesting the twin adapter with the first RE, resulting in two adapters with the same restriction fragment end; digesting a genomic DNA with at least a second restriction enzyme ("second RE"), wherein the digestion by the second RE results in the genomic DNA being broken into a plurality of restriction fragments, wherein the second RE has a recognition site different from that of the first RE, yet after digestion leaves the same restriction fragment end as that of the first RE; ligating with a DNA ligase the adapter to the plurality of restriction fragments, resulting in a mixture of a self-ligation product and a hetero-ligation product, wherein the first RE or the second RE can cleave the self-ligation product and is incapable of cleaving the hetero-ligation product; repeating the ligating and digesting steps, to make the adapter-tagged restriction library substantially free of the self-ligation product.

In one embodiment, the method can be used to determine the global methylation percentage of a genomic DNA, comprising: providing a genomic DNA sample; making one reference restriction library and one target restriction library according to the method, wherein the second RE is used in the target restriction library and is methylation-sensitive, wherein a third RE is used in the reference restriction library and is methylation-insensitive, wherein the methylation-sensitive second RE and the methylation-insensitive third RE have the same restriction site and leave the same restriction fragment end; providing a universal primer whose sequence is complementary to the adapter and the newly formed sequence in hetero-ligation in the method; separately amplifying the target and the reference restriction libraries with a quantities PCR system; determining the methylation percentage by calculating the restriction fragment number between the target and reference restriction libraries.

In another embodiment, each RE can be used as the second RE, wherein combining REs produce the restriction library with shorter restriction fragments and more restriction fragments. In another embodiment, the restriction fragment number in the restriction library can be quantified by qPCR (quantitative polymerase chain reaction).

In another embodiment, the percentage of methylation of the genomic DNA is determined by qPCR (quantitative polymerase chain reaction). In another embodiment, the calculating method of the percentage of genomic DNA methylation is ddCT method in real-time PCR. In another embodiment, the percentage of genomic DNA methylation is directly calculated by a digital PCR instrument. In another embodiment, the ligation between adapter and restriction fragment in making restriction library is performed with a DNA ligase.

In another embodiment, wherein the DNA ligase is T4 DNA ligase. In another embodiment, the first RE is methylation sensitive RE. In another embodiment, the first RE is Cla I. In another embodiment, the second RE is a 4-base cutter. In another embodiment, the second RE in target restriction library is Hpa II. In another embodiment, the third RE in reference restriction library is Msp I. In another embodiment, at least 20 connective base pair sequence around the first RE recognition site is the same between the two strands of the twin adapter. In another embodiment, the twin adapter comprises a designed palindromic sequence. In another embodiment, the two strand sequences of the twin adapter are the same. In another embodiment, the twin adapter sequence is a self-pairing DNA nucleotide sequence of SEQ ID NO: 1:

```
                                           (SEQ ID NO: 1)
5' CGATCGACCTCTAGGCTTCAGACAGATCGATCTGTCTGAAG
CCTAGAGGTCGATCG 3'

(SEQ ID NO: 1 in 3' to 5' orientation)
3' GCTAGCTGGAGATCCGAAGTCTGTCTAGCTAGACAGACTTC
GGATCTCCAGCTAGC 5'
```

DETAILED DESCRIPTION

Figure 1:
FIG. 1 is a diagram showing a restriction fragment ligated with the adapter.

The present application relates to methods of tagging restriction library. As explained in further details below, genomic DNA are often broken down (or cut) into smaller pieces to be manipulated and studied. Among different methods of cutting the genomic DNAs into smaller pieces, only digestion by restriction enzymes can get the same fragments among repeated experiments.

Restriction enzymes recognize a specific sequence of nucleotides and produce a double-stranded cut in the DNA. These recognized specific sequence of nucleotides sites are called restriction sites. Restriction enzymes cut DNA at or near the recognitions sites. More specifically, to cut DNA, all restriction enzymes make two incisions, once through each sugar-phosphate backbone (i.e. each strand) of the DNA double helix.

There are four main types of restriction enzymes, type I, II, III and IV. The four types differ in their structure and where they cut relative to their recognition sites. Type II restriction enzymes recognize and cleave DNA at precisely the same site.

Type II restriction enzymes usually have undivided recognition sites that are palindromic and 4-8 nucleotides in length. For example, type II restriction enzyme Eco RI recognize the following restriction site, with the upper strand from left to right in 5' to 3' orientation and the lower strand from left to right in 3' to 5' orientation:

As shown by the line in the Eco RI recognition site above, Eco RI cut between the G and A in the upper strand and between A and G in the lower strand. Consequently, a restriction fragment end after the Eco RI cutting (on the lower strand) has a "TTAA" tail that is single stranded. Such restriction fragment ends are commonly referred to as an "overhang". And, because the single-stranded tail can pair with other compatible single-stranded DNA, the ends harboring such a tail is also commonly referred to as "sticky" ends. Restriction fragments produced by digesting a genomic DNA with one restriction enzyme share the same sticky ends with the same overhang. Some type II restriction enzymes cut both strands of their recognition sites at the same location and produce "blunt ends" instead of sticky ends.

In addition to the large sizes of the genomic DNAs, another obstacle of studying is the limited quantity of the genomic DNAs, especially when the genomic DNAs are isolated from limited supply of subject tissues or primary cell culture. As a result it is often important to be able to amplify the limited quantity of the genomic DNAs. Since (as mentioned above) genomic DNAs are often cut into restriction fragments for easier manipulation and study. One of the ways to amplify the restriction fragments is to add short known sequences to the ends of the restriction fragments and then amplify the restriction fragments with primers that are complementary to the added known sequences. The added known sequence oligonucleotide is often referred to as "adapter." And the process of adding the known sequences is referred to as "tagging."

Adding the adapters to the restriction fragments is achieved via ligation. In molecular biology ligation often refers to a reaction joining two nucleic acid fragments through the action of an enzyme. Ligation is often performed using the enzyme T4 DNA ligase. However, other DNA ligases can be used and procedures for ligation without the use of standard DNA ligase are also popular.

Type II restriction enzyme cut DNA double strand and leave the 5' end a phosphate and the 3' end a hydroxyl groups. As described above, restriction enzymes can leave 2 overhangs after cutting a genomic DNA into restriction fragments. The single-stranded overhang can be compatible (i.e., capable of pairing with) other overhangs produced by the same restriction enzyme or certain other restriction enzymes. The process of compatible overhangs pairing with each other is often referred to as "annealing." Some restriction enzymes can also leave "blunt ends" after digestion. "Blunt ends" refers to restriction fragment ends where both strands terminate at the same base pair. The "blunt ends" can be ligated to any other "blunt ends", although such ligation is not as efficient as a sticky end ligating to a compatible sticky end.

T4 DNA Ligase catalyzes the joining of two strands of DNA between the 5'-phosphate and the 3'-hydroxyl groups of adjacent nucleotides when compatible (and paired) restriction fragment ends annealing together. More specifically, T4 DNA ligase catalyze a synthesis of phosphodiester bond between the 3' hydroxyl of one nucleotide and 5' phosphate of another. Through such catalysis T4 DNA Ligase can join adapters and restriction fragment ends.

As described above, adding adapters to the restriction fragments is one way to amplify the restriction library (thereby amplify the genomic DNA where the restriction fragments come from) for manipulation and study. Reliable ligation between the adapters and the restriction fragments (in order to faithfully amplifying the restriction fragments)

is the basis for subsequent steps. Yet traditionally the hetero-ligation efficiency has been a challenge to ligate the adapters and the restriction fragments.

Part of the challenge to reliably ligate the adapters and the restriction fragments results from the self-ligation between the restriction fragments and the self-ligation of the adapters. This is so because in studying the genomic DNA it is often important to know the accurate number of restriction fragments produced by a given restriction enzyme. The number and the size of restriction fragments reflect the number and location of the recognition sites of the given restriction enzyme. The number and location of the recognition sites are often important parameters in mapping the genomic DNA. The self-ligation of the restriction fragments masks the true number and location of recognition sites of the given restriction enzyme, thereby interferes with mapping of the genomic DNA.

Traditional ligation methods were not able to avoid the self-ligation problem. This is so because traditional methods were unable to distinguish the undesired self-ligation products among the restriction fragments (and adapters) themselves and the desired hetero-ligation products between the restriction fragments and the adapters. More specifically, self-ligated restriction fragments (which contains two or more true individual restriction fragments) can further ligate with adapters and be amplified in subsequent steps. As such the amplified self-ligated restriction fragments competes with and mask the amplified true individual restriction fragments.

To make the problem worse for traditional methods, the ligation among the restriction fragments and the adaptors are essentially random event. That is, the extent of the undesired self-ligation varies from experiments to experiments. In other words, the ratio among the three types of ligation (restriction fragment-restriction fragment self-ligation, adaptor-adaptor self-ligation and the hetero restriction fragment-adaptor ligation) varies among different experiments even with identical samples. The unpredictable variation of the extent of self-ligation means that traditional methods cannot compensate for the interference caused by the undesired self-ligation. Consequently the undesired self-ligations would interfere and cause fatal flaws to the downstream genomic DNA analysis based on the number of restriction fragments. To be sure, attempts have been made to decrease restriction fragment-restriction fragment self-ligations, such as increasing the ratio of adaptors in the reaction mixture. However, these attempts only marginally solve the problem and cannot at all fully avoid the self-ligation problem. As a result, self-ligation remains a technical barrier which makes it difficult to analyze genomic DNAs by comparing the number and size of restriction fragments between genomic DNAs (or within the same genomic DNA under different conditions).

The methods disclosed in the present application overcome the self-ligation problem by distinguishing the undesired self-ligation products from the desired hetero-ligation products. As disclosed, the present inventor was able to think outside the box of the traditional approaches to utilize different restriction enzymes to cut the genomic DNA and to create the adapters. Some restriction enzymes have different recognition sites but leave the same overhang after digestion. As a result, the adapters can ligate with the restriction fragments via their common overhang. Yet, once ligated, the junction between the adapter and restriction fragment is no longer a recognition site for any of the restriction enzyme used to create the restriction fragments or the adapters. Unlike the hetero-ligation products between the adapters and the restriction fragments, the self-ligation products among the restriction fragments themselves (or the adapter themselves) recreate the recognition sites of the restriction enzyme used to create the restriction fragments or the adapters. The methods disclosed in the present application utilize such difference between the hetero-ligation products and the self-ligation products to create pure (and desired) hetero-ligation products for downstream analysis of the genomic DNA.

One of the approaches to create pure hetero-ligation products is to eliminate the self-ligation products from the reaction mixture. One of the ways to eliminate the self-ligation products is to repeat digestion of the self-ligation products and ligate them with adapters. As described above, the self-ligation recreates the recognition sites for the restriction enzyme, the repeated digestion recuts the self-ligation products into individual restriction fragments or individual adapters. In practice, the repeat ligation and digestion can be performed multiple times as needed to eliminate the self-ligation products, in order to create pure hetero-ligation products between the restriction fragments and the adapters. As such, the disclosed methods avoid restriction fragment-restriction fragment and adapter-adapter self-ligation. Consequently, all ends of the restriction fragments are tagged with the adapters, which make it possible to get consistent restriction fragment numbers from the same sample among different experiments.

Being able to eliminate self-ligation of the restriction fragments (and thereby enabling precise and reliable analysis of the restriction fragments) can help improve various genomic DNA analyses. One such example is the analysis of methylation of genome DNA.

DNA methylation is a biochemical phenomenon where a methyl group is added to the cytosine or adenine in DNA. Cytosine is methylated at the 5-carbon position producing a moiety called 5-methylcytosine. In mammals, genome DNA methylation occurs at the cytosine-phosphate-guanine sites, or a CpG dinucleotide. About 90% of all CpGs are methylated in mammals. DNA methylation plays an essential role for normal gene expression, X inactivation, genomic imprinting, developmental biology, aging, and diseases. More specifically, DNA methylation alters gene expression in cells when cells divide and differentiate.

It is important to study DNA methylation due to its physiological and pathological importance. In general there are two ways to study DNA methylation, gene-specific DNA methylation and "global" methylation across the whole genomic DNA. Gene-specific DNA methylation analysis is a common methodology to detect gene methylation. However, it is difficult for gene-specific methylation analysis to find untargeted loci changes. Additionally, gene-specific methylation analysis is unable to provide whole picture of DNA methylation changes across genomic DNA. Moreover, gene-specific methylation analysis is limited to the predetermined genes, thereby cannot identify new biomarkers. In contrast, global methylation analysis can lead to identification of new disease biomarkers related to the diagnosis and therapy of cancer, diabetes as well as rheumatoid arthritis.

Yet the effort to study global DNA methylation is limited by technical inability to obtain whole genomic DNA methylation profile. Several methods have been developed to measure global methylation, but numerous drawbacks exist. For example, bisulfite conversion based high throughput methods such as next generation sequencing and microarray are time consuming, costly, imprecise and unreliable.

Bisulfite conversion based methods also suffer from possible bisulfate conversion errors, which either inappropriately convert 5-methylcytosine to thymine, or fail to convert unmethylated cytosine to uracil. Other methods, such as 5-methyl-cytosine immuno-precipitation based methods, suffer from substantial variation within and among different methods. Consequently, in basic research and clinical applications, there is an urgent need in the field to overcome the disadvantages of these methods, in order to advance the technologies for measuring global methylation. The disclosed methods are unique and have been developed partially for the reason to overcome the technical limitations stated above.

As explained above, accurate measurement of methylation level depends on accurately breaking down the genomic DNAs into fragments and subsequently amplifying them in a faithful fashion. In addition to the shortcomings suffered by current methods, such as bisulfite conversion based methods and 5-methyl-cytosine immuno-precipitation based methods, traditional methods also suffer because of the inaccuracies in the breaking down and amplifying the genomic DNA. As described above, such inaccuracies are partially caused by the self-ligation of the broken-down fragments (called restriction fragments). The methods disclosed in the present application, in part, take advantage of the facts that: (1) some restriction enzymes (e.g., restriction enzymes X and Y) can have difference recognition sites yet leave the same sticky ends and same overhang, and (2) some restriction enzymes (e.g., restriction enzymes Y and Z) can have exact same recognition sites, but only differ in that one restriction enzyme is affected by methylation and the other is not. In the field restriction enzymes that is affected by methylation are often referred to as being methylation-sensitive (MSRE), while restriction enzymes that are not affected by methylation are often referred to as being methylation-insensitive (MIRE). For example, here restriction enzyme Y can be methylation-sensitive while restriction enzyme Z can be methylation-insensitive, despite the fact that they both recognize the same restriction site.

More specifically, the disclosed methods in the present application create restriction fragments from a genomic DNA using restriction enzyme X, and create adapters using restriction enzyme Y. Because X and Y leave the same ends, restriction fragments can ligate with adapters. But upon restriction fragment-adapter ligation, such a hetero-ligation product is no longer recognizable by either X or Y. On the other hand, the restriction fragment-restriction fragment self-ligation product is still recognizable by X. And the adapter self-ligation product is still recognizable by Y. The disclosed methods in the present application take advantage of such distinction and treat the restriction fragment-adapter ligation reaction mixture with X and Y. Because the self-ligation products are recognizable by X and Y, the treatment by X and Y break down the self-ligation products back to individual restriction fragments or individual adapters. Repeating the ligation and digestion, the self-ligation products become fewer and fewer until disappearing from the reaction mixture. Then all ligation products are hetero-ligation products in the end. In the subsequent amplification steps, the individual restriction fragments or individual adapters will not amplify unless they ligate to each other to form hetero-ligation products. As such the disclosed methods in the present application is able to distinguish self-ligation products and hetero-ligation products, thereby eliminating the self-ligation products to select only hetero-ligation products for analysis.

As mentioned above, in addition to taking advantage of the fact that some restriction enzymes can have difference recognition sites yet leave the same ends, the methods disclosed in the present application also take advantage of the fact that some restriction enzymes can have exact same recognition sites, but only differ in that one kind of restriction enzyme is affected by methylation and the other is not. More specifically, the disclosed methods in the present application can measure methylation level at restriction site. For example, when the same genomic DNA is separately digested with methylation insensitive restriction enzyme and methylation sensitive restriction enzyme the methylation insensitive restriction enzyme produce more fragments than methylation sensitive restriction enzyme. Quantifying the digestion products of the two enzymes provides indications of the methylation level of the genomic DNA.

In addition to determine the methylation level of one genomic DNA, the methods disclosed in the present application can also: (1) compare the methylation levels of different tissue or organs of a given organism, (2) compare the methylation of the same tissue or organs from different individuals.

Quantitative PCR has become the gold-standard method for accurate quantification of nucleic acids. Relative quantification is based on internal reference genes to determine the expression of target genes.

The Delta CT method is one of the relative quantitation methods to calculate real-time PCR result. For instance, using the example above, two restriction enzymes MSRE and MIRE digesting the same genomic DNA produce different number of restriction fragments. Using the Ct value in real-time PCR, the restriction fragment number differences between the two restriction libraries can be determined. The restriction fragment number difference between the MSRS-produced restriction library and MIRE-produced restriction library accurately indicates the number of methylation percentage in the recognition site, which MIRE can cut but MSRE cannot cut.

Digital polymerase chain reaction (digital PCR, or dPCR) is a refinement of conventional polymerase chain reaction methods. Real-time PCR carries out one reaction per single sample, while dPCR carries out a single reaction within a single DNA molecular. Using dPCR, the methylation percentage of a restriction library can be directly counted by a dPCR instrument.

One example of restriction enzyme with different recognition sites but leaving same overhang upon digestion is Cla I and Msp I (or Hpa II). Cla I recognize the following site:

```
(upper strand)
5'-AT/CGAT-3'

(lower strand)
3'-TAGC/TA-5'
```

Cla I cuts between the T and C in the upper strand, and between the C and T in the lower strand.
Upon cutting, Cla I leaves an overhang as follows:

```
(upper strand)
5'-AT-3'

(lower strand)
3'-TAGC-5'
```

Msp I (or Hpa II) recognize the following site:

```
(upper strand)
5'-C/CGG-3'

(lower strand)
3'-GGC/C-5'
```

Msp I (or Hpa II) cuts between the two Cs in the upper strand and the two Cs in the lower strand.
Upon cutting, Msp I (or Hpa II) leaves an overhang as follows:

```
(upper strand)
5'-C-3'

(lower strand)
3'-GGC-5'
```

As can be seen, even though Cla I and Msp I/Hpa II have different recognition site, upon digestion they leave the same 3'-GC-5' overhang. As a result, the fragment ends of Cla I digestion can anneal to the fragment ends of Msp I/Hpa II digestion, and be subsequently ligated together. As described above, the hetero-ligation product (5'-ATCGG-3') is no longer recognizable by either Cla I or Msp I/Hpa II, but the self-ligation products of Cla I and the self-ligation products of Msp I/Hpa II can be re-cut, such distinction between the hetero-ligation product and self-ligation products can be utilized to eliminate self-ligation products and select hetero-ligation products for better genomic DNA analysis.

Msp I and Hpa II provides one example of two restriction enzymes having exact same recognition sites but differing in methylation sensitivity. Specifically, Hpa II only recognizes the unmethylated CCGG sequence and is unable to cut methylated CCGG sequence. On the other hand, Msp I recognize and is able to cut both methylated and unmethylated CCGG sequence.

EXAMPLES

The disclosed methods in the present application are illustrated by way of the following examples and figures referred to therein. As such the examples and figures are for illustration purpose only and do not limit in any way the disclosed methods in the present application.

Example 1

The polymerase chain reaction (PCR) is one of the most sensitive and most reliable methods so far to quantify the DNA template number. The quantity of the target DNA doubles during each amplification cycle. In this example, Cla I is used as the first RE to cut a "twin adapter" to create two adapters. The two strand sequence of the twin adapter is palindromic and same as shown below:

```
                                      (SEQ ID NO: 1)
5' CGATCGACCTCTAGGCTTCAGACAGATCGATCTGTCTGAAG
CCTAGAGGTCGATCG 3'

(SEQ ID NO: 1 in 3' to 5' orientation)
3' GCTAGCTGGAGATCCGAAGTCTGTCTAGCTAGACAGACTTC
GGATCTCCAGCTAGC 5'
```

Msp I (methylation-insensitive) enzyme is used as the second RE to create a restriction library from a genomic DNA with the method mentioned above. The restriction fragment ends in the restriction library are then ligated to the two adapters. FIG. 1 is a diagram showing a restriction fragment ligated with two adapters. As can be seen, the junction sequence between the restriction fragments and the adaptor formed a new sequence 5'-ATCGG no longer recognizable by either Cla I (recognition site 5'-ATCGAT) or Msp I (recognition site 5'-CCGG). The one strand of adapter ending with the newly-formed sequence after hetero-ligation can be used as universal primer (The primer sequence: 5'-CGATCGACCTCTAGGCTTCAGACAGATCGG-3').

Using the universal primer to run PCR can specifically amplify the tagged restriction fragments in the restriction library. That is, only the hetero-ligation products can survive further Cla I and Msp I digestion, and be amplified in further steps. As such, the method in this example avoids self-ligation among restriction fragment themselves and adapter themselves. Consequently identical samples will always produce consistent numbers of restriction fragments. Such consistency is crucial for systematic analysis of the genomic DNA via the restriction fragments.

Example 2

Tagged restriction library making system includes five reagents beside the DNA sample:
1. DNA Twin adaptor, a synthesized double strand DNA-Oligo with a palindromic sequence comprising a 6-base cutter (Cla I) recognition site in the middle. The two DNA strand sequences in the twin adapter are identical and palindromic sequence. The twin adapter will become two adaptors after being cleaved by the 6-base cutter in step 2 below.
2. A 6-base cutter, Cla I, is used to cleave the twin adaptor to generate adaptors. Because Cla I cuts the genomic DNA much less frequently than Msp I or Hpa II, thereby barely interfere with the methylation measurement.
3. A 4-base cutter, Msp I or Hpa II, is used to cleave the genomic DNA. Msp I or Hpa II cannot cleave the twin adaptor.
4. T4 DNA ligase to join the restriction fragments and the adaptors.
5. A universal buffer for the restriction enzymes and T4 ligase.

Global methylation quantitation system includes two reagents beside restriction library:
a. A polymerase master mix for qPCR, All tested commercial products work
b. A universal primer, mentioned above The number of restriction fragments in the methylation-insensitive-enzyme-produced restriction library is more than that of the methylation-sensitive-enzyme-produced restriction library. After double-stranded DNA adaptors are added to the ends of the restriction fragments, qPCR can measure the restriction fragment ratio between Msp I-produced and Hpa II-produced restriction library using the universal primer mentioned above. The ratio represents the percentage of global methylation at restriction site CCGG sequence, which is proportional to the amount of CpG (1/16) in the whole genomic DNA.

The following steps are performed to create (including amplify) the restriction library, and measure methylation level:
1. Add equal amount of a genomic DNA into two tubes containing the Msp I restriction library making system or Hpa II restriction library making system.

2. Incubate the two tubes in PCR instrument. Repeat the following thermal cycle 100 times: 22 degree Celsius for 2 minutes, 16 degree 2 minutes, and 4 degree 2 minutes.

The following digestion and ligation occurs during the thermal cycles:

At 22 degree, genomic DNA is cleaved by Msp I or Hpa II to generate restriction fragments. As the same time, Cla I cleaves the twin adapter show below to generate two adaptors.

```
                                          (SEQ ID NO: 1)
5' CGATCGACCTCTAGGCTTCAGACAGATCGATCTGTCTGAAG
   CCTAGAGGTCGATCG 3'

(SEQ ID NO: 1 in 3' to 5' orientation)
3' GCTAGCTGGAGATCCGAAGTCTGTCTAGCTAGACAGACTTC
   GGATCTCCAGCTAGC 5'
```

Hpa II, Msp I and Cla I have more than 75% activity left at 22 degree. The generated restriction fragments and adaptors have the compatible CG-5' overhang that contain phosphate at 5' ends. At 4 degree Celsius, the compatible overhangs anneal together then T4 DNA ligases join the two annealed ends.

Figure 2:
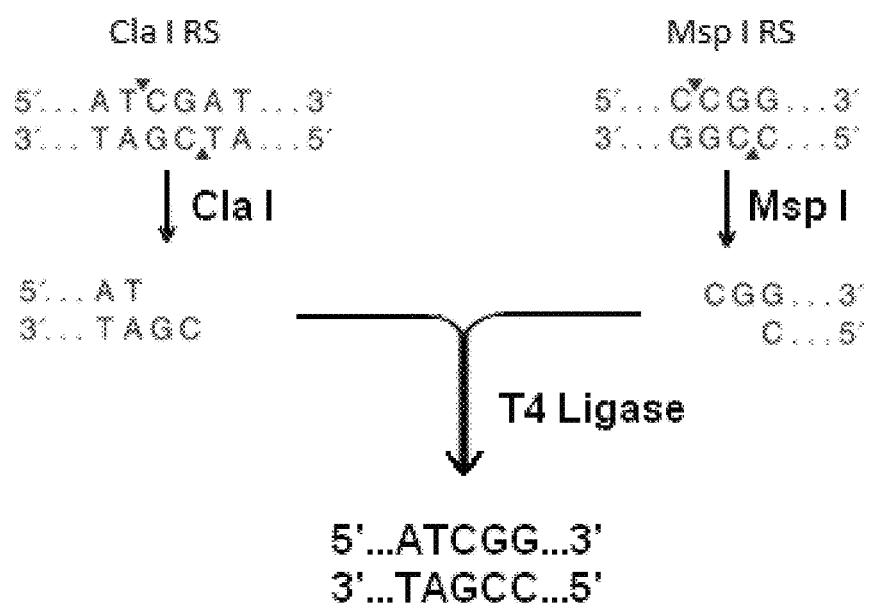
FIG. 2 is a diagram showing that, once a restriction fragment (here resulting from a cut by Msp I) is ligated with an adapter (produced via digestion by Cla I), the ligated product is no longer recognizable by either Cla I or Msp I.

3. As shown in FIG. 2, the hetero-ligation between adaptors and restriction fragments form a new sequence around the overhang. Consequently the hetero-ligation is no longer recognizable by Cla I, Msp I or Hpa II.

Figure 3:
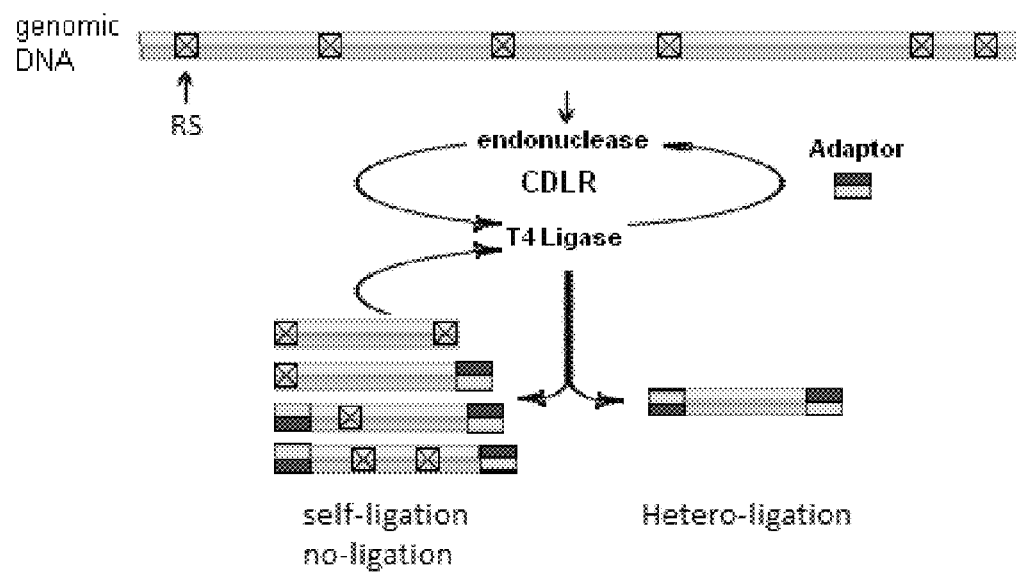
FIG. 3 is a diagram demonstrating hetero-ligation (where adapters are ligated to restriction fragments), self-ligation (where restriction fragments ligate to each other, or adapters ligate to each other) and no-ligation (where restriction fragments are neither ligated to adaptors, nor ligated to each other) in a cycle digestion-ligation reaction.

4. As shown in FIG. 3, unlike the hetero-ligation products, the restriction sites of non-digested genomic DNA, non-ligated restriction fragments or adapters (where restriction fragments are neither ligated to adaptors, nor ligated to each other), and self-ligated restriction fragments or adapters will recycle to the next digestion-ligation cycle.

5. The proportion of hetero-ligation products becomes higher and higher, while the proportion of self-ligation products becomes lower and lower accompanied with repeating the cycle digestion-ligation reaction.

6. All restriction sites in the Msp I restriction library making system disappear after hetero-ligation between restriction fragments and the adapters at reaction end, but not the methylated restriction sites (CCGG) in Hpa II restriction library making system.

7. To inactivate T4 DNA ligase and cut the self-ligation products that may have formed after finishing the cycle digestion-ligation reaction, continue digestion at 37 degree Celsius for 2 hours in PCR instrument.

8. Run qPCR with the two restriction libraries generated as described above. The restriction fragments tagged with adaptors are amplified in qPCR.

Figure 4:
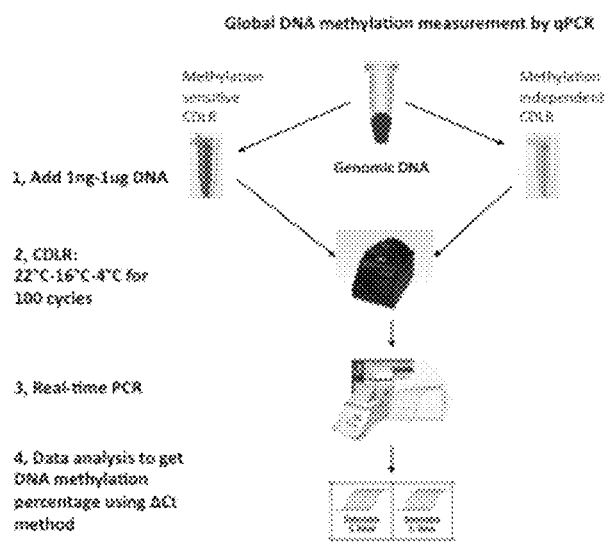
FIG. 4 is a diagram showing a work flow chart depicting the steps in measuring the methylation level of a genomic DNA.

9. Perform data analysis to determine global methylation percentage using the delta CT method. FIG. 4 is a diagram showing a work flow chart depicting the steps in measuring the methylation level of a genomic DNA.

10. Note: The percentage of hetero-ligation between Cla I and Hpa II (Msp I) fragments is dependent of Cla I restriction site and methylation percentage in DNA samples. In other words, it is the global methylation percentage at Cla I restriction site. Because the Cla I is methylation sensitive and restriction site much less than Msp I (Hpa II), it is negligible generally.

Counting restriction sites in human genomic DNA, there are 2,296,918 Msp I restriction sites (CCGG) and only 85,091 ClaI restriction sites (ATCGAT) in the human genomic DNA. Cla I also is a methylation-sensitive restriction enzyme. About 90% Cla I site were methylated generally, so only 8509/2296918=0.37% hetero-ligation come from Cla I restriction fragments in the Msp I restriction library making system. Similarly the hetero-ligation between Cla I and Hpa II fragment will be 4% around in the Hpa II restriction library making system.

Example 3

Check the Restriction Fragment Tagging Efficiency

Figure 5:
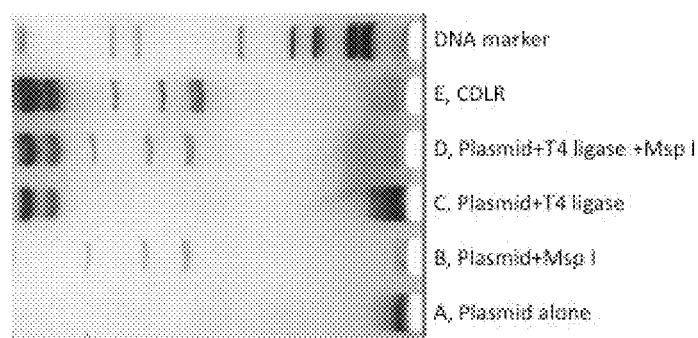
FIG. 5 is a picture showing successful ligation of the adapters with the restriction fragments without self-ligation among the restriction fragments themselves.

In this example, a plasmid (used as a genomic DNA) is digested into restriction fragments. The efficiency of these restriction fragments being tagged with adapters is tested. This example is illustrated in FIG. 5, which shows successful ligation of the adapters with the restriction fragments without self-ligation among the restriction fragments themselves. Specifically, a plasmid was incubated overnight then loading on 8% non-denatured PAGE gel. The gel is stained with silver nitrate. In lane A (undigested plasmid alone), all plasmid stacked at the edge of the well because it's size too big. Lane B (plasmid plus Msp I), showed restriction fragments after Msp I digestion. Lane C (plasmid plus T4 ligase) showed the T4 ligase and no restriction fragments. Lane D, (plasmid+T4+MspI), showed that the restriction fragment size is the same as the restriction fragments size in lane B. Lane E includes Msp I, T4 ligase, plasmid, and the adaptor, for the adapters to be tagged to the restriction fragments produced from the plasmid being digested by Msp I. The result showed that the tagged restriction fragment bands are sharp and that the bands' size increased, comparing with lane B and D (both with the adapters). The increased size means that the adaptors were tagged to the restriction fragments and that there is no self-ligation of the restriction fragments.

Example 4

Check PCR Products from the Restriction Library

Figure 6:
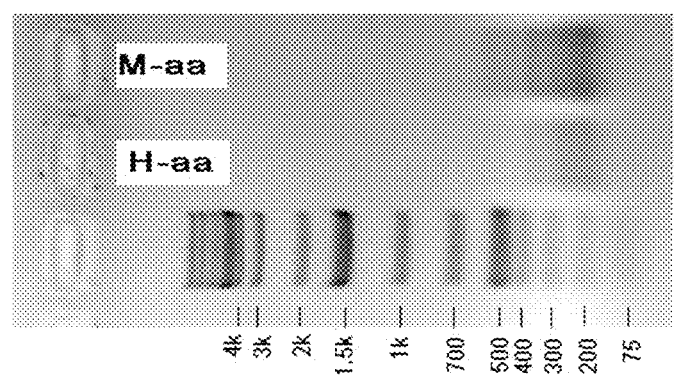
FIG. 6 is a picture showing that methylation-sensitive restriction enzyme Hpa II, as expected, generate fewer products (i.e., cut less frequently) than its counterpart methylation-insensitive restriction enzyme Msp I.

This example is illustrated in FIG. 6, which is a picture showing that methylation-sensitive restriction enzyme Hpa II, as expected, generate fewer products (i.e., cut less frequently) than its counterpart methylation-insensitive restriction enzyme Msp I. Specifically, qPCR with Msp I restriction library (lane M-aa) or Hpa II restriction library (lane H-aa) made from a human genomic DNA. 15 ul qPCR product is loaded on 1.5% agarose gel. As expected, the methylation-sensitive Hpa II (which cannot cut methylated sites) has fewer products than the methylation-insentive Msp I (which can cut regardless of methylation) at 22nd cycle.

Example 5

Check qPCR Standard Curve and Efficiency

Figure 7:
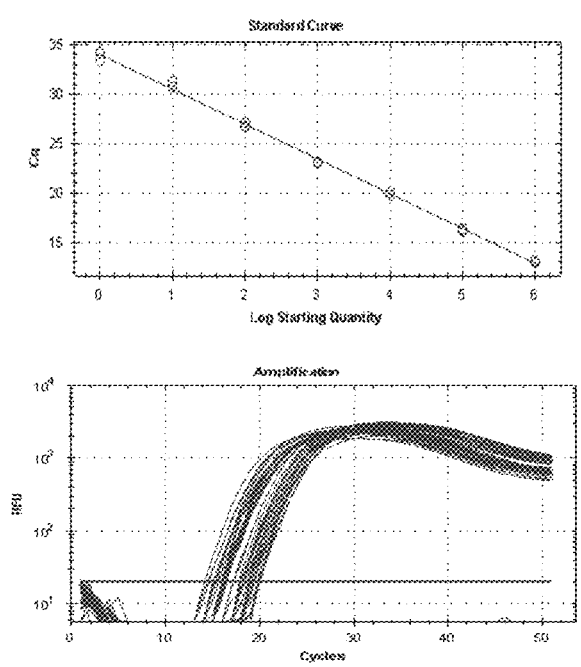
FIG. 7 shows the qPCR (quantitative PCR) standard curve and that qPCR efficiencies are the same between the Msp I-digested restriction fragments and the Hpa II-digested restriction fragments.

This example is illustrated in FIG. 7, which showed the qPCR standard curve and that qPCR efficiencies are the same between the Msp I restriction library and the Hpa II restriction library. Specifically, in FIG. 7 the upper picture is the qPCR standard curve. The starting DNA is 1.0 ng from MspI restriction library, serial dilutions of 10 times ranging from 1.0 ng to 0.001 pg. The PCR efficiency is 99.97% and R square=0.998. The bottom picture shows that qPCR efficiencies are the same in both Msp I and Hpa II restriction library.

Example 6

Check Methylation in Different Organs

Figure 8:
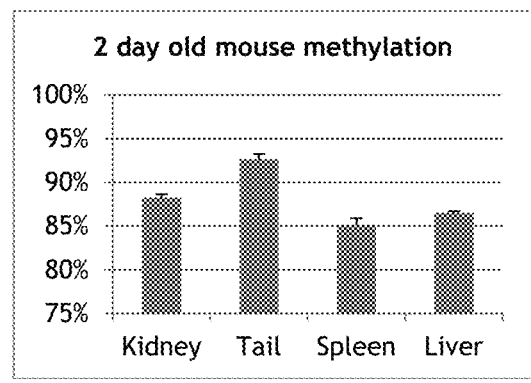
FIG. 8 is a diagram showing that methylation levels differ among different organs from C57BL/6 mice.

This example is illustrated in FIG. 8, which is a diagram showing that methylation levels differ among different organs from C57BL/6 mice (kidney, tail, spleen and liver).

Specifically, the genomic DNA samples were isolated from 2-day-old C57BL/6 mice. The result showed that the disclosure method used to check the small but significant differences of global methylation percentage among different organs.

Example 7

Check the Effect of Methylation Inhibitor

Figure 9:
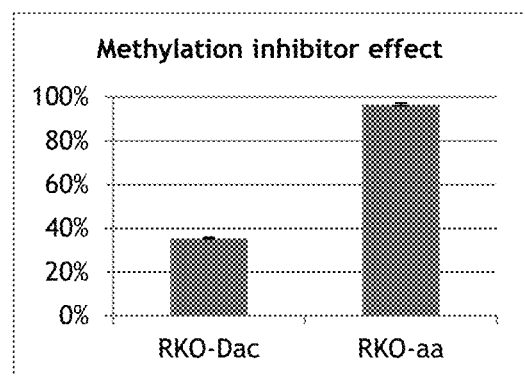
FIG. 9 is a diagram showing that the methods disclosed in the present application are able to detect that methylation inhibitor DAC significantly affected the methylation level of RKO cell line.

This example is illustrated in FIG. 9, which is a diagram showing that the methods disclosed in the present application are able to detect that drug effect on the global methylation level. Specifically, RKO cell line was cultured using standard methods. Cells were treated with methylation inhibitor 5 μM 5-aza-2' deoxycytidine (DAC) for 3 days prior to being harvested. The result showed that methylation percentage of RKO cells decreased from 96.7% to 35.6% after methylation inhibitor (DAC) treatment.

Measurement of global DNA methylation is cumbersome at present. It is often prohibitively costly, inaccurate and unreliable, and it needs large amount of samples. The disclosed methods in the present application are robust, accurate, sensitive, simple, and fast. The disclosed methods can be used to measure percentage of the global methylation within a single cell genomic DNA. Consequently the disclosed methods are the only methods that enable researchers to study global methylation changes in stem cell in different developmental stages and treatment effect. The disclosed methods are capable of identifying 0.5% of global methylation difference between samples. None of the existing methods is capable of doing so. In addition to the improved accuracy and sensitivity, the disclosed methods only take researcher a few hours to directly measure and analyze global methylation analysis in DNA samples.

All references cited in the description are hereby incorporated by reference in their entirety. While the disclosure has been described with respect to a limited number of embodiments, those skilled in the art, having benefit of this disclosure, will appreciate that other embodiments can be advised and achieved which do not depart from the scope of the description as disclosed herein.

SEQUENCE LISTING

```
<160> NUMBER OF SEQ ID NOS: 1

<210> SEQ ID NO 1
<211> LENGTH: 56
<212> TYPE: DNA
<213> ORGANISM: Artificial Sequence
<220> FEATURE:
<223> OTHER INFORMATION: the artificial sequence is used to generate
      some of the adapters to be tagged to the ends of restriction
      fragments, thereby enabling precise amplificaiton of the
      restriction fragments

<400> SEQUENCE: 1
cgatcgacct ctaggcttca gacagatcga tctgtctgaa gcctagaggt cgatcg        56
```

What is claimed is:

1. A method of making an adapter-tagged restriction library comprising:
    providing a double-stranded DNA oligonucleotide which is a twin adapter containing a recognition site of a first restriction enzyme (first RE);
    digesting the twin adapter with the first RE, resulting in two adapters with the same restriction fragment end;
    digesting a genomic DNA with at least a second restriction enzyme (second RE), wherein the digestion by the second RE results in the genomic DNA being broken into a plurality of restriction fragments, wherein the second RE has a recognition site different from that of the first RE, yet after digestion leaves the same restriction fragment end as that of the first RE;
    ligating with a DNA ligase the digested twin adapter to one end or each end of the plurality of restriction fragments, resulting in a mixture of a self-ligation product and a hetero-ligation product;
    repeating the ligating and digesting steps multiple times as needed with the mixture of a self-ligation product and a hetero-ligation product, to make the adapter-tagged restriction library substantially free of the self-ligation product, wherein the repeated digesting step is the step of digesting the mixture of a self-ligation product and a hetero-ligation product with the first RE or the second RE, wherein the first RE or the second RE can cleave the self-ligation product and is incapable of cleaving the hetero-ligation product, and wherein the repeated digesting and ligating steps result in the hetero-ligation product substantially free of the self-ligation product.

2. A method of determining the global methylation percentage of a genomic DNA, comprising:
providing a genomic DNA sample;
making one reference restriction library and one target restriction library according to the method of claim 1, wherein the second RE is used in the target restriction library and is methylation-sensitive, wherein a third RE is used in the reference restriction library and is methylation-insensitive, wherein the methylation-sensitive second RE and the methylation-insensitive third RE have the same restriction site and leave the same restriction fragment end;
providing a universal primer whose sequence is complementary to the digested twin adapter and the newly formed sequence in hetero-ligation in claim 1;
separately amplifying the target and the reference restriction libraries with a quantitative PCR system;
determining the methylation percentage by calculating the restriction fragment number between the target and reference restriction libraries.

3. The method of claim 1, wherein each RE can be used as the second RE, wherein combining REs produce the restriction library with shorter restriction fragments and more restriction fragments.

4. The method of claim 1, wherein the restriction fragment number in the restriction library can be quantified by qPCR (quantitative polymerase chain reaction).

5. The method of claim 2, wherein the percentage of methylation of the genomic DNA is determined by qPCR (quantitative polymerase chain reaction) technique.

6. The method of claim 2, wherein the calculating method of the percentage of methylation of genomic DNA fragments in the libraries is delta CT method.

7. The method of claim 2, wherein the percentage of genomic DNA methylation is directly calculated by a digital PCR instrument.

8. The method of claim 1, wherein the ligation between the adapter and the restriction fragment in making restriction library is performed with a DNA ligase.

9. The method of claim 8, wherein the DNA ligase is T4 DNA ligase.

10. The method of claim 2, wherein the first RE is a methylation sensitive RE.

11. The method of claim 2, wherein the first RE is Cla I.

12. The method of claim 2, wherein the second RE is a 4-base cutter.

13. The method of claim 12, wherein the second RE in target restriction library is Hpa II.

14. The method of claim 2, wherein the third RE in the reference restriction library is a 4-base cutter.

15. The method of claim 14, wherein the second RE in the reference restriction library is Msp I.

16. The method of claim 1, wherein an at least 20 connective base pair sequence comprising the first RE recognition site is the same between the two strands of the twin adapter.

17. The method of claim 1, wherein the twin adapter comprises a designed palindromic sequence.

18. The method of claim 2, wherein the two strand sequences of the twin adapter are the same.

19. The method of claim 2, wherein the twin adapter sequence is a self-pairing DNA nucleotide sequence of SEQ ID NO: 1:

```
                                          (SEQ ID NO: 1)
5' CGATCGACCTCTAGGCTTCAGACAGATCGATCTGTCTGAAG
CCTAGAGGTCGATCG 3'

(SEQ ID NO: 1 in 3' to 5' orientation)
3' GCTAGCTGGAGATCCGAAGTCTGTCTAGCTAGACAGACTTC
GGATCTCCAGCTAGC 5'.
```

* * * * *